US012754406B2

(12) United States Patent
Bourbon et al.

(10) Patent No.: US 12,754,406 B2
(45) Date of Patent: Oct. 6, 2026

(54) STEREOSCOPIC ASSEMBLY, SURGICAL MICROSCOPE WITH STEREOSCOPIC ASSEMBLY, AND SURGICAL SET

(71) Applicant: Scholly Fiberoptic GmbH, Denzlingen (DE)

(72) Inventors: Johannes Bourbon, Freiburg (DE); Julian Nehlich, Freiburg (DE)

(73) Assignee: Schoelly Fiberoptic GmbH, Denzlingen (DE)

( * ) Notice: Subject to any disclaimer, the term of this patent is extended or adjusted under 35 U.S.C. 154(b) by 85 days.

(21) Appl. No.: 18/843,353

(22) PCT Filed: Feb. 20, 2023

(86) PCT No.: PCT/EP2023/054248
§ 371 (c)(1),
(2) Date: Sep. 3, 2024

(87) PCT Pub. No.: WO2023/165842
PCT Pub. Date: Sep. 7, 2023

(65) Prior Publication Data

US 2025/0199280 A1 Jun. 19, 2025

(30) Foreign Application Priority Data

Mar. 3, 2022 (DE) ......................... 102022105089.0
Mar. 3, 2022 (DE) ......................... 102022105090.4

(51) Int. Cl.
*G02B 21/00* (2006.01)
*A61B 1/00* (2006.01)
(Continued)

(52) U.S. Cl.
CPC ...... *G02B 21/0012* (2013.01); *A61B 1/00045* (2013.01); *A61B 1/00188* (2013.01);
(Continued)

(58) Field of Classification Search
CPC .. G02B 21/0012; G02B 21/22; G02B 21/361; A61B 1/00193; A61B 1/00188; A61B 1/00045; A61B 34/30
See application file for complete search history.

(56) References Cited

U.S. PATENT DOCUMENTS 7,057,807 B2 6/2006 Sander
2007/0121203 A1 5/2007 Riederer
(Continued)

FOREIGN PATENT DOCUMENTS

CN 101266333 A 9/2008
DE 4336715 A1 4/1994
(Continued)

OTHER PUBLICATIONS

Claus Daniel et al "Focus and perspective adaptive digital surgical microscope: optomechanical design and experimental implementation", Journal of Biomedical Optics. 1000 20th Si Bellingham WA 98225-6705 USA, vol. 22, 13 pages, No. 05, May 25, 2017 (May 25, 2017).

*Primary Examiner* — Georgia Y Epps
*Assistant Examiner* — Don J Williams
(74) *Attorney, Agent, or Firm* — Volpe Koenig

(57) ABSTRACT

A stereoscopic arrangement that includes each of at least one objective unit, a deflection unit and at least one image sensor. In this case, a sub-path is intended to be aligned such that a projection of the same sub-path along a projection direction onto a first sub-path of the same optical path is oriented counter to the first sub-path. In addition, in the case of a stereoscopic arrangement, it is provided for an image sensor to be arranged in a half-space that is delimited by an auxiliary plane containing a deflection unit and aligned orthogonally to the first sub-path of the optical path (8, 108)
(Continued)

and contains the objective unit. A surgical microscope having such a stereoscopic arrangement is also provided.

20 Claims, 9 Drawing Sheets

(51) Int. Cl.
*A61B 34/30* (2016.01)
*G02B 21/22* (2006.01)
*G02B 21/36* (2006.01)

(52) U.S. Cl.
CPC .......... *A61B 1/00193* (2013.01); *A61B 34/30* (2016.02); *G02B 21/22* (2013.01); *G02B 21/361* (2013.01)

(56) References Cited

U.S. PATENT DOCUMENTS

| | | | | |
|---|---|---|---|---|
| 2016/0266369 | A1* | 9/2016 | Hauger .................. | G02B 21/22 |
| 2017/0115477 | A1 | 4/2017 | Kiening et al. | |

FOREIGN PATENT DOCUMENTS

| | | | |
|---|---|---|---|
| DE | 102005030346 | B9 | 4/2008 |
| DE | 102008041819 | A1 | 3/2010 |
| DE | 102009019575 | A1 | 11/2010 |
| DE | 102009021087 | B4 | 3/2015 |
| DE | 102014108811 | B3 | 11/2015 |
| DE | 102017110816 | A1 | 7/2018 |
| EP | 1460466 | B1 | 9/2004 |
| JP | H11318936 | A | 11/1999 |

* cited by examiner

STEREOSCOPIC ASSEMBLY, SURGICAL MICROSCOPE WITH STEREOSCOPIC ASSEMBLY, AND SURGICAL SET

CROSS-REFERENCE TO RELATED APPLICATIONS

This application is a 371 National Phase of PCT/EP2023/054248, filed Feb. 20, 2023, which claims priority from German Patent Application No. 10 2022 105 089.0, filed Mar. 3, 2022, and German Patent Application No. 10 2022 105 090.4, filed Mar. 3, 2022, all of which are incorporated herein by reference as if fully set forth.

TECHNICAL FIELD

The invention relates to a stereoscopic arrangement that implements a stereoscopic imaging system, having an objective unit, a deflection unit, a lens arrangement and an image sensor unit. The stereoscopic arrangement may in particular comprise at least one objective unit, at least one deflection unit and at least one image sensor. In this case, the image sensor is arranged downstream of the at least one deflection unit with respect to an optical path beginning at a stereoscopic base.

The invention furthermore relates to a surgical microscope having such a stereoscopic arrangement.

Finally, the invention also relates to a surgical kit that is able to be used in surgical interventions and that comprises a stereoscopic arrangement that is attached to a movable robot arm and is able to be pivoted in space with the aid of the robot arm. The arrangement is in this case preferably designed in accordance with the invention.

BACKGROUND

Such stereoscopic arrangements and surgical microscopes are used for example in surgical interventions. In this case, the patient is observed using such an arrangement or such a microscope. The surgeon stands next to the patient and looks at a monitor on which the stereoscopic image that was recorded, or is currently being recorded live, using the stereoscopic arrangement is shown to them.

However, the space available for such an arrangement in the vicinity of the patient is highly limited since the surgeon's view of the monitor has to be clear, and also the operating space below the stereoscopic arrangement and above the patient has to remain freely accessible. The space able to be taken up by such an arrangement is therefore highly limited.

This is particularly the case when the viewing angle of the stereoscopic arrangement is to be changed. In this case, the arrangement, which is attached to a tripod, may be pivoted about one or more axes. As already mentioned, the arrangement may be attached to a robot arm so as to be able to pivot, for example about two axes. This pivoting may result in the surgeon's view of the monitor being obstructed, in particular when pivoting takes place about an axis running parallel to the distance between the two visual beams, the stereoscopic base.

In systems known to date, it is generally the case that the image beams or optical paths are deflected by a deflection unit. An optical path may be considered to be split into multiple sub-paths by the deflection unit. For instance, by way of example, one sub-path runs between the stereoscopic base and the deflection unit, and one sub-path runs between the deflection unit and the image sensor unit. An optical path may also be broken down into more than two sub-paths. In systems known to date, the deflection generally takes place such that the optical paths are deflected out of the plane occupied by the two first sub-paths such that the further sub-paths (used for stereoscopic imaging) lead away from the surgeon or even lead into the line of sight from the surgeon to the monitor and may thus obstruct them in certain situations.

SUMMARY

The invention is based on the object of providing a stereoscopic arrangement and a surgical microscope having a stereoscopic arrangement the space requirements of which are reduced to such an extent that the stated problems are able to be reduced or even completely avoided. In particular, the intention here is for ergonomics to be improved when working with a surgical kit, as described at the outset, during a medical procedure.

In order to achieve the stated object, one or more of the features disclosed hereon are provided according to the invention. In particular, in order to achieve the stated object in stereoscopic arrangements of the type described at the outset, it is thus provided, according to the invention, for a first sub-path and a further sub-path of the optical path to be aligned with one another such that a projection of the further sub-path along a projection direction onto the first sub-path is oriented counter to the first sub-path.

The sub-paths may thus be oriented such that they do not protrude into the line of sight of the surgeon to the monitor. On the contrary, the sub-paths may be guided away in the lateral direction, as will be explained in more detail.

By way of example, the first sub-path may run here from the objective unit to the deflection unit.

As an alternative or in addition, provision may be made for the further sub-path to be arranged downstream of the deflection unit and/or to end at the image sensor unit.

In one advantageous embodiment, provision may be made for the projection direction to be aligned at an angle, in particular orthogonally and/or in an angular range of ±45° to an orthogonal direction, to the first sub-path of the optical path.

A further sub-path is thus at least partially reflected from a deflection unit in the direction of the origin of the optical path in the stereoscopic base and does not protrude into the line of sight of the surgeon to the monitor.

As an alternative or in addition to the features explained above, in order to achieve the stated object, additional ones of the features disclosed herein are provided according to the invention. In particular, in order to achieve the stated object in stereoscopic arrangements of the type described at the outset, it is thus provided, according to the invention, for the image sensor to be arranged in a half-space containing the objective unit, the half-space being delimited by an auxiliary plane containing the deflection unit and aligned orthogonally to the first sub-path of the optical path.

The image sensor is therefore not located closer to the surgeon's line of sight to the monitor than a deflection unit. This thus reduces or avoids impairment of the surgeon's view of the monitor. This is particularly the case in the event of the viewing direction being inclined, that is to say for example when the optical axis of the objective unit adopts an angle to a surface normal of the operating area currently being observed with the stereoscopic arrangement.

In one advantageous embodiment, provision may be made for the auxiliary plane to run through a point of incidence of the optical path on the deflection unit. The half-space in which the image sensor may be located is thereby narrowed. This thus reduces the structural height of the stereoscopic arrangement. This thus reduces or avoids impairment of the surgeon's view of the monitor.

One preferred embodiment makes provision for two optical sub-paths to be formed, these running from the at least one deflection unit to a respective image sensor (wherein these sub-paths may be used directly for stereoscopic imaging). A respective optical lens or lens group is in this case arranged in each of these two sub-paths, specifically in a manner spaced from the at least one deflection unit and spaced from the respective image sensor. In this case, the position and/or orientation of the optical lens or lens group relative to the associated deflection unit and relative to the associated image sensor is designed to be adjustable. This may subsume the following two cases: Either a respective setting means (for example an adjusting screw or a settable lens holder) is formed so as to adjust the position and/or orientation of the respective optical lens or lens group; or a position and/or orientation, which is adjusted and optimized once, of the respective optical lens or lens group has been/is permanently fixed; by way of example, the lens or lens group may be adjusted during assembly as the last optical component and then fixed in the optimal position once this has been found.

In both cases, the provided adjustment of the lens/lens group makes it possible to optimize imaging in the respective sub-path. This is because it turned out, in practice, that for example the position of the two image sensors cannot be controlled precisely as desired, often resulting in an aberration in the form of a "defocus" or distortion. This is particularly the case if a respective separate deflection unit is also formed for each sub-path, this then also having to be individually aligned and positioned. By adjusting the lens or lens group, it is thus possible in particular to compensate for manufacturing tolerances, that is to say for instance fluctuations in the thickness of the glasses of the lenses or deflection elements that are used or other fluctuations in the shape of the lenses, and thus to achieve in each case a sharp image in the respective beam path of the respective optical sub-path of the stereoscopic imaging system.

In one advantageous embodiment, provision may be made for at least two deflection units to be aligned such that their deflection angles define the same direction of rotation.

The optical path may thus for example run in a U-shape and/or be reflected counter to the alignment of its first sub-path.

In one advantageous embodiment, provision may be made for at least one lens group of a lens arrangement, preferably a lens arrangement containing displaceable and/or changeable lens groups, to be formed in an optical path between a deflection unit and an objective unit and/or an image sensor.

In one advantageous embodiment, provision may also be made for at least one lens group of a lens arrangement, preferably a lens arrangement containing displaceable and/or changeable lens groups, to be formed in a sub-path running in the auxiliary plane.

It is thus possible to integrate a lens arrangement that changes the image section or defines a focal plane into the stereoscopic arrangement in order to meet the respective requirements at the usage location of the stereoscopic arrangement. By way of example, a lens arrangement defining a focal plane may be formed between an objective unit and a deflection unit and/or a lens arrangement changing the image section may be formed within the auxiliary plane, for example between a deflection unit and an image sensor. It is thus possible to implement an afocal system in which a change in the image section is not accompanied by a change in the focal plane.

The respective lens arrangements for changing the image section and/or for changing the focal plane may be formed in a manner spaced from one another. The respective lens arrangements may also be separated from one another by a deflection unit. The lens groups may consist of one or more lenses, the lenses of a lens group may contact one another or be formed in a manner spaced from one another. By way of example, provision may be made for a respective spacer. A lens group is able to be displaced without changing the distance between the lenses that it contains. By way of example, a lens group may be changeable by virtue of the distance between the lenses that it contains being able to be changed in relation to one another.

In one advantageous embodiment, provision may be made for a lens arrangement to form a zoom lens. In such an embodiment, it is preferable for a deflection unit to be located between at least two lens groups of this lens arrangement/this zoom lens. This deflection unit thus connects two optical sub-paths that run through the zoom lens, but in different spatial directions.

In particular, at least one lens group of this lens arrangement/of this zoom lens may be located in a sub-path, running away from the auxiliary plane, of an optical path and at least one lens group of this lens arrangement/of this zoom lens may be located in a sub-path, running towards the auxiliary plane, of an optical path. The optical path within the zoom lens is thereby divided into different directions, wherein deflection of the optical path within the zoom lens is able to be achieved by way of the deflection unit. The lens arrangement forming the zoom lens is thereby able to be arranged in a space-saving manner, even in the case of a complex design with numerous optical lenses, by breaking down the zoom lens (conceptually) into multiple components that are placed in a respective sub-path. In such an approach, however, it is not possible to resort to compact zoom lenses previously known in the prior art, because these typically have a uniform housing and a consistently straight optical axis. The approach according to the invention breaks up such a system and distributes the individual optical components of the zoom lens among optical sub-paths that run in different spatial directions. As a result, the line of sight is thus able to be kept clear better for the surgeon.

In one advantageous embodiment, provision may be made for at least one separate objective unit and/or deflection unit and/or lens group of a lens arrangement and/or image sensor to be provided for each optical path.

Differences in optical path lengths are thus easily able to be compensated for. This may also be achieved by displacing individual lens groups of one or both optical paths. By way of example, the components formed in one optical path may be fixed in terms of their position, and the lens groups of the other path may be moved. Using separate lens groups for both paths may advantageously be used to eliminate unfavorable peripheral rays and/or stray light.

In one advantageous embodiment, provision may also be made for at least one common objective unit and/or deflection unit and/or lens group of a lens arrangement and/or image sensor to be provided for the optical paths. This enables easy installation.

This thus makes it possible, depending on the requirements, in particular depending on the space available for optical components or their desired alignment in space, to provide separate components for each optical path. However, common components may also be provided for both optical paths. By way of example, a focus unit upstream of a first deflection unit may be configured with common lens groups and a zoom lens downstream of the first deflection unit may be configured with separate lens groups for each of the two optical paths. The deflection unit may be configured to be common to both paths and/or separate for each path.

In one advantageous embodiment, provision may be made for at least one beam splitter to be located in at least one optical path, in particular wherein a separate image sensor is arranged in each sub-beam leaving the beam splitter.

The image sensors are thus able to be placed in an advantageous manner. Multiple image sensors may also be provided for each optical path. By way of example, the same optical path, namely the sub-beams thereof, could be observed with image sensors tuned to different spectral regions.

Finally, a (common) focus unit upstream of a first deflection unit may also be configured with common lens groups and/or a zoom lens downstream of the first deflection unit may be configured with separate lens groups for each of the two optical paths. The deflection unit may be configured to be common to both paths and/or separate for each path.

The focus unit may have at least one tunable focus lens by way of which it is possible to change a focus plane of the stereoscopic arrangement. The term "tunable" may be understood here to mean that the refractive power and/or the position of the focus lens is able to be changed along the optical axis. In this case, objects that are located in the current focus plane are imaged sharply onto the at least one image sensor, such that the focus plane forms the object plane of the respective imaging beam path formed by the respective optical path of the stereoscopic arrangement, while the image plane coincides with an active surface of the at least one image sensor. The distance between the focus plane/object plane that is currently set (with the aid of the changeable focus unit) and the at least one objective unit (in particular a first lens surface of this objective unit) may in this case be understood as a working distance. By way of example, if a working distance of 15 cm is set, then objects that are at located at this distance in front of the objective unit are imaged sharply onto the respective image sensor. Different working distances may thus be made possible with the aid of the focus unit (by tuning the focus lens).

Provision may thus be made for at least one focus unit to be formed, which focus unit is arranged upstream of the at least one deflection unit in the beam path and by way of which focus unit it is possible to change a position of a focus plane of the stereoscopic arrangement.

The focus unit may in this case preferably be formed in particular by a lens group and/or in each case as part of the at least one objective unit.

The focus unit is in this case preferably placed such that incident uncollimated imaging beams of the respective optical path leave the focus unit in collimated form and then impinge on the at least one deflection unit as collimated light. Within the stereoscopic arrangement, the focus unit may thus assume the optical function of converting uncollimated incoming light beams (coming from said focus plane/the object under observation) into collimated light.

Such a focus unit may also be designed separately for both optical paths, preference being given to a common focus unit because, in the latter case, it is necessary to drive only one tunable lens, and not to drive two lenses synchronously.

In order to improve the use characteristics of the arrangement, it is also advantageous to provide a variable aperture stop, preferably in each case in each of the two paths used for stereoscopic vision. This thus makes it possible to arrange at least one adjustable aperture stop downstream of the at least one objective unit in the beam path, using which aperture stop it is possible to adjust a depth of field and/or an optical resolution. If two optical paths are formed running from the at least one deflection unit to a respective image sensor, then it makes sense for a respective adjustable aperture stop to then be arranged in each of these two optical paths.

One preferred application of the invention makes provision for a stereoscopic arrangement according to the invention, in particular as described above, to be used in a surgical microscope or an endoscope or an exoscope.

In order to solve the problem stated at the outset and thus in order to improve the ergonomics and use characteristics of a stereoscopic arrangement according to the invention, the invention provides a specific surgical kit, that is to say a spatial arrangement of the following components: The surgical kit according to the invention, which may be used in particular in surgical interventions, for instance for observing an operating area on or in the body of a patient, comprises:

- a stereoscopic arrangement having one or more of the features as described herein. In this case, the stereoscopic arrangement may be designed for example as part of a surgical microscope or of an endoscope or of an exoscope;
- a screen for displaying a stereoscopic image (that is to say in particular for displaying a stereoscopic image data stream, for instance in the form of a live video) that has been recorded or is being recorded with the stereoscopic arrangement. The screen may in this case preferably be arranged behind the stereoscopic arrangement such that a surgeon looking at the screen (in order thus to observe a patient with the aid of the arrangement) has a clear view of the screen. In other words, this thus makes it possible to provide a clear line of sight to the screen for a surgeon, or such a line of sight may be kept clear for a surgeon; preferably, the line of sight in this case runs orthogonally to a display surface of the screen and ends in this display surface.

Finally, the surgical kit comprises a (movable) robot arm (for instance as part of a complex surgical robot), wherein the stereoscopic arrangement is attached to the robot arm and is thus able to be pivoted with the robot arm in space, preferably about two different axes. With the aid of the robot arm, it is thus possible to change a viewing angle of the stereoscopic arrangement. This is because, when the robot arm moves, the stereoscopic arrangement moves as well, wherein a spatial position and/or orientation of an optical axis of the at least one objective unit (and thus the viewing direction of the stereoscopic arrangement) and/or a distance between the at least one objective unit and an object/operating area to be observed (and thus the working distance of the stereoscopic arrangement) are/is then able to be changed.

In order to achieve the object, provision is made, according to the invention, for the stereoscopic base of the arrangement to run parallel to the screen and for the optical paths of the arrangement, that is to say in particular the sub-paths between the at least one deflection unit and the respective image sensor, to be guided away parallel to the stereoscopic base and to the side (with respect to a clear line of sight between the surgeon and the screen).

Such a surgical kit may reduce the burden on the surgeon, especially in the case of difficult microsurgical procedures, wherein the respective carrying along of the stereoscopic arrangement on the robot arm and in particular the changeable focus plane thereof (this being adjustable with the aid of the described focus unit) allows the surgeon to always be shown the desired spatial impression of the current operating area with the aid of the stereoscopic arrangement in different situations with an excellent image sharpness on the screen. With the aid of the described at least one aperture stop, the surgeon is also able here to adapt the resolution and the depth of field of the recorded stereo images as they wish.

The stated advantages, in particular with regard to the reduced space requirement of such a stereoscopic arrangement, are thus able to be implemented in a surgical microscope and used during a medical intervention.

BRIEF DESCRIPTION OF THE DRAWINGS

The invention will now be described in more detail with reference to exemplary embodiments, but is not restricted to the exemplary embodiments. Further exemplary embodiments will become apparent by combining the features of one or more claims with one another and/or with one or more features of the exemplary embodiment.

In the figures.

DETAILED DESCRIPTION

Components and functional units that are functionally and/or structurally similar or identical to preceding exemplary embodiments are designated with the same reference signs and not described again separately in each case. The explanations regarding FIG. 1 thus apply accordingly to the following figures.

Figure 1:
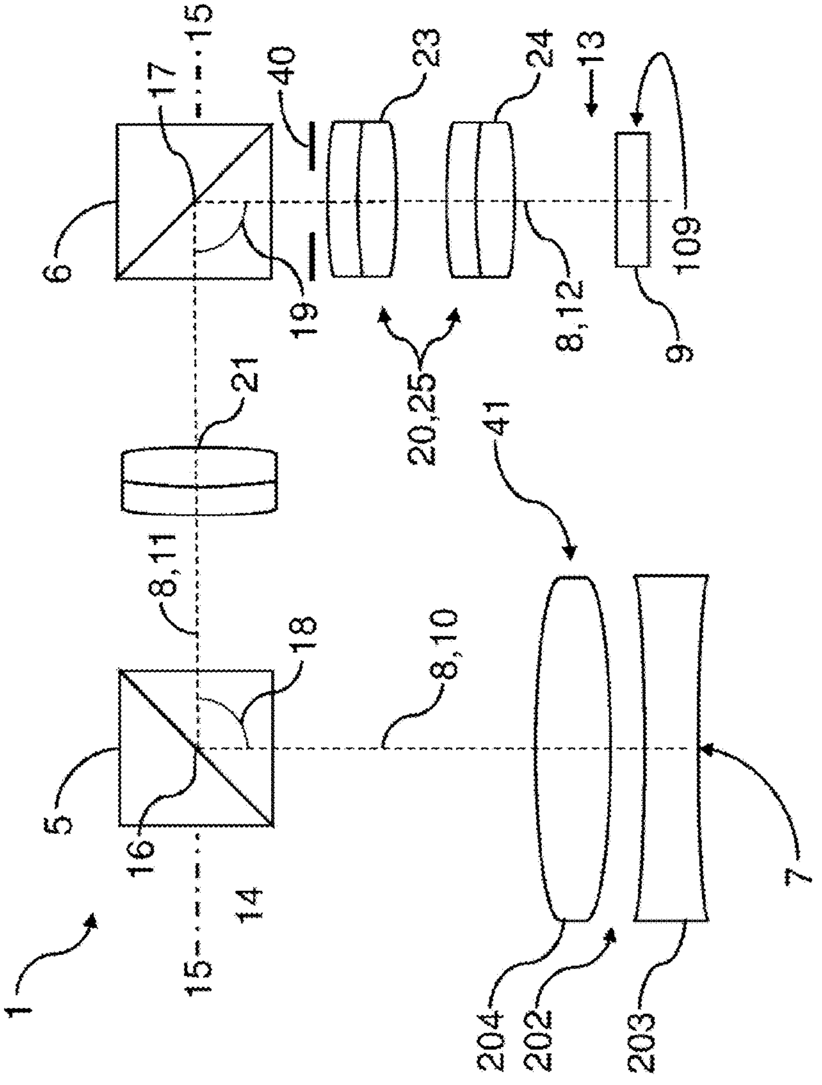
FIG. 1 shows a side view of a stereoscopic arrangement according to the invention.

FIG. 1 shows a side view of a stereoscopic arrangement 1 having a common objective unit 202, consisting of common lens groups 203, 204, and two deflection units 5, 6.

The common lens groups 203, 204, like all of the other lens groups as well, may consist of individual but also multiple lenses. The lenses and/or lens groups may be connected to one another and/or separated from one another by an air gap, for example using a spacer. To adjust the focal plane, for example, a lens group 203 may be displaced relative to a lens group 204. An optical path 8 beginning at the stereoscopic base 7 runs via the objective unit 202 and the deflection units 5, 6 to an image sensor 9.

The viewing direction of the stereoscopic arrangement 1 is in this case directly counter to the direction of the first sub-path 10; in other words, the arrangement 1 is able to receive imaging beams from a spatial direction corresponding to the direction of the sub-path 10 and thus record images in the viewing direction.

Figure 2:
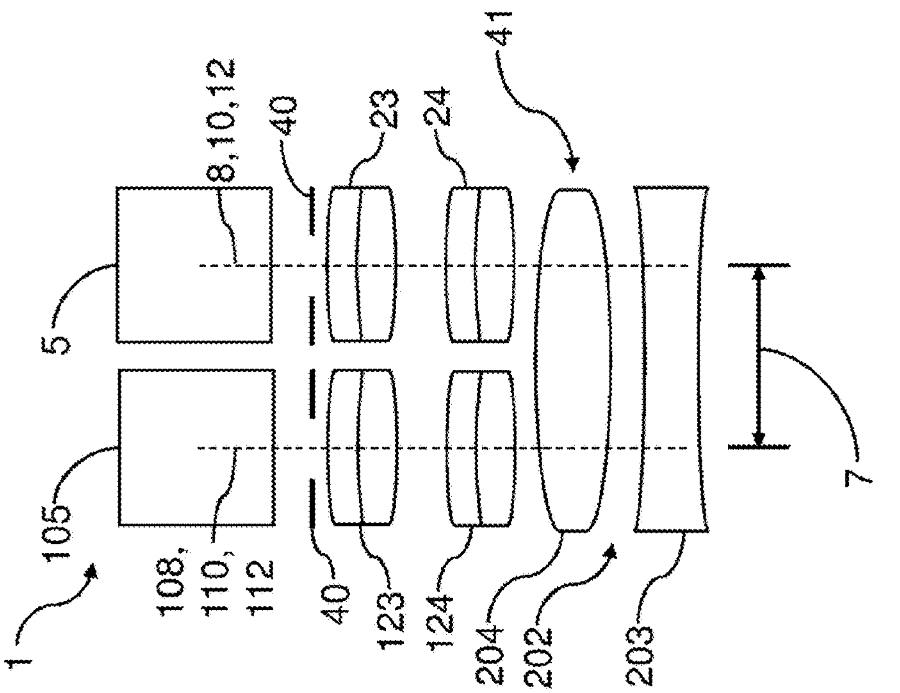
FIG. 2 shows a frontal view of the stereoscopic arrangement from FIG. 1.

An optical path 108 runs parallel to the optical path 8 (see FIG. 2). By way of example, a second image sensor 109 for the optical path 108 is thus positioned downstream of the image sensor 9. The image sensor 109 is obscured by the image sensor 9 in FIG. 1. The optical path 8 may be considered to be divided into a first sub-path 10 and two further sub-paths 11, 12 by the deflection units 5, 6. It becomes clear here that a projection of the further sub-path 12 onto the first sub-path 10 along a projection direction 13 images the further sub-path 12 onto the first sub-path 10 in a manner oriented counter thereto. Furthermore, in this exemplary embodiment, the projection direction 13 is aligned orthogonally to the first sub-path 10.

The image sensor 9, and also the image sensor 109, are located here in a half-space 14 containing the objective unit 202 and delimited by an auxiliary plane 15 containing the deflection unit 5 and oriented orthogonally to the first sub-path 10. In this exemplary embodiment, the auxiliary plane 15 contains a point of incidence 16 of the optical path 8 on the deflection unit 5.

In this exemplary embodiment, the deflection units 5, 6 are aligned such that their deflection angles 18, 19 define the same direction of rotation, in the clockwise direction in the view that is shown.

The lens groups 23, 24 form a lens arrangement 20, which forms a zoom lens 25. The two lens groups 23, 24 are located in the sub-path 12 of the optical path 8, between the deflection unit 6 and the image sensor 9. The entire zoom lens 25 is thus arranged here in the optical path 12, which runs directly counter to the viewing direction of the arrangement 1, that is to say counter to the direction of the first optical sub-path 10.

The deflection unit 6 is located between the lens groups 21 and 23. It would also be conceivable for the lens group 21 to belong to the lens arrangement 20 and/or to the zoom lens 25, such that the lens arrangement 20 and/or the zoom lens 25 would extend over the deflection unit 6 and in two sub-paths 11 and 12. Such an embodiment is shown for example in FIGS. 3 and 5, wherein, here as well, as already in FIG. 1, at least part of the zoom lens 25 (namely here for example the lens groups 23 and 24) is arranged in the optical path 12 that runs directly counter to the viewing direction of the arrangement 1, that is to say counter to the direction of the first optical sub-path 10.

FIG. 2 shows a frontal view of the stereoscopic arrangement 1 from FIG. 1. In addition to the components belonging to the optical path 8, it is possible to see the optical path 108, guided parallel to the optical path 8, containing the associated deflection unit 105 and the lens groups 123, 124.

Figure 3:
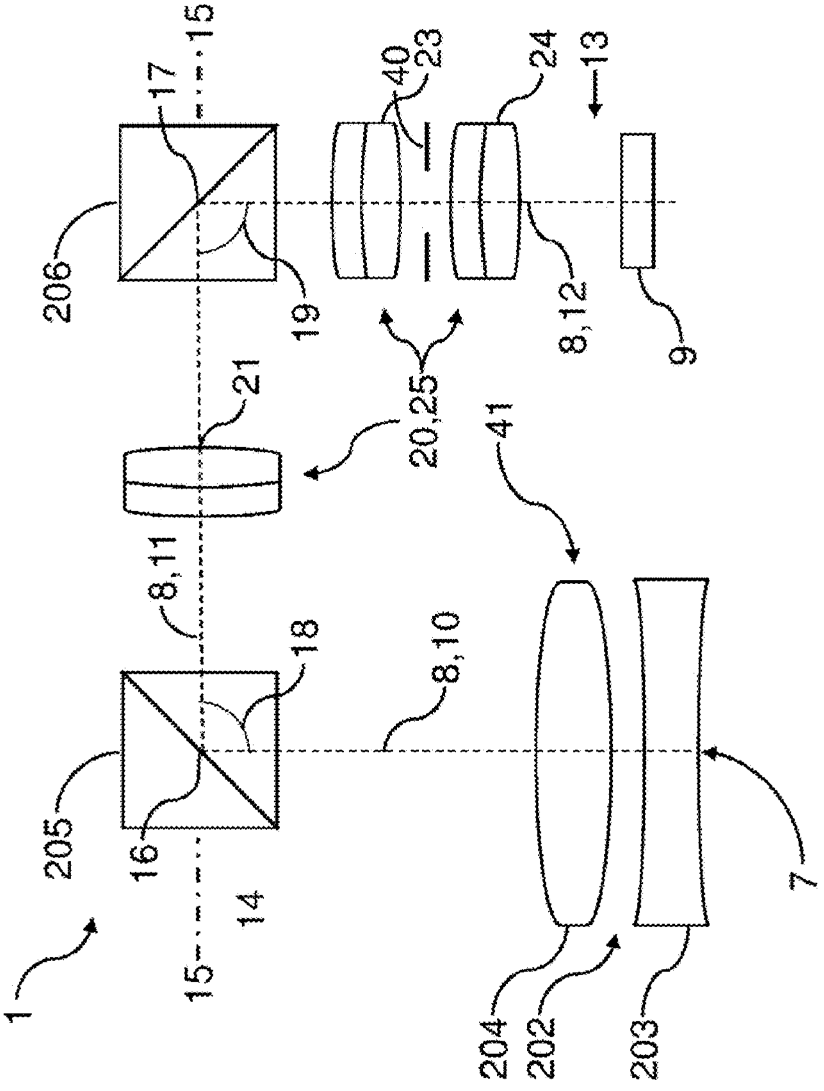
FIG. 3 shows a side view of a stereoscopic arrangement according to the invention.

FIG. 3 shows a side view of a further stereoscopic arrangement 1 according to the invention, which differs from the stereoscopic arrangement 1 shown in FIG. 1 at least in that, instead of separate deflection units 5, 6, 105, 106, in this exemplary embodiment, common deflection units 205 and 206 are formed. The lens arrangement 20 and the zoom lens 25 also extend over the common deflection unit 206.

Figure 4:
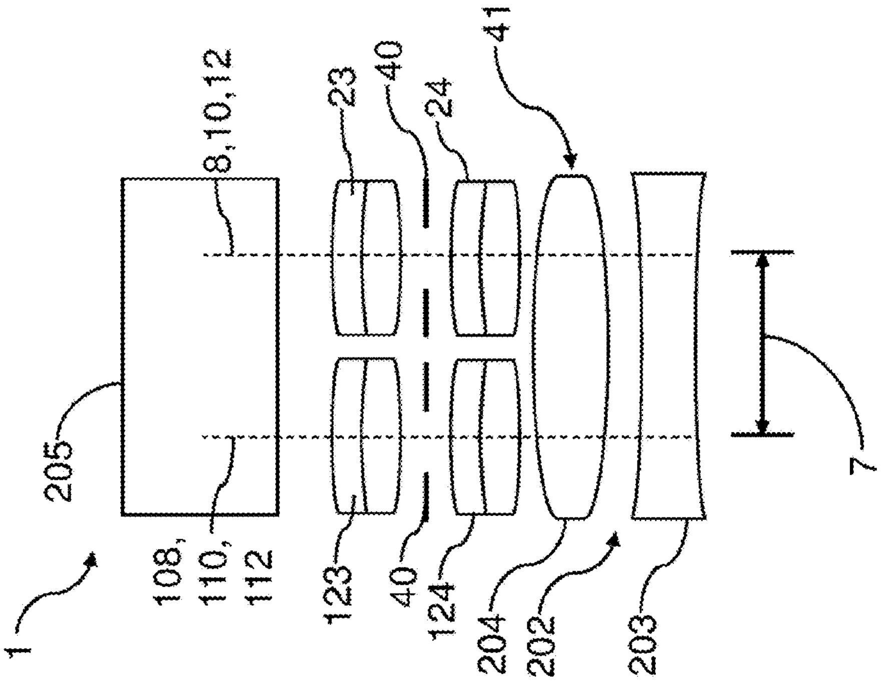
FIG. 4 shows a frontal view of the stereoscopic arrangement from FIG. 3.

FIG. 4 shows a frontal view of the stereoscopic arrangement from FIG. 3, wherein the common deflection unit 205 may in particular be seen. It obscures the further common deflection unit 206 in this view. It is also possible to see the common objective unit 202 having common lens groups 203, 204 and lens groups 23, 24, 123, 124 that are implemented separately for each optical path 8, 108.

Figure 5:
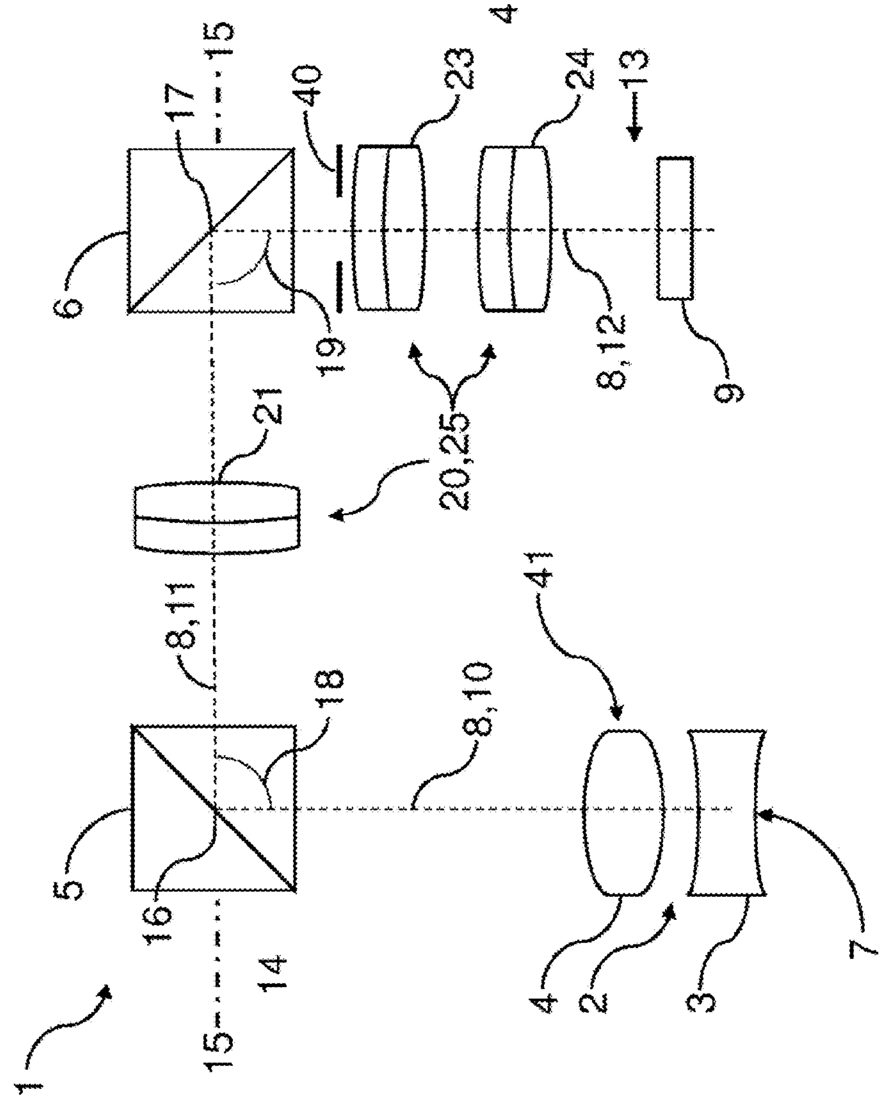
FIG. 5 shows a side view of a stereoscopic arrangement according to the invention.

FIG. 5 shows a side view of a further stereoscopic arrangement 1 according to the invention. In particular, the deflection units 5, 6, 105, 106 are configured as separate elements for each optical path 8, 108. Separate objective units 2, 102 having separate lens groups 3, 4, 103, 104 are also provided for each optical path 8, 108.

Figure 6:
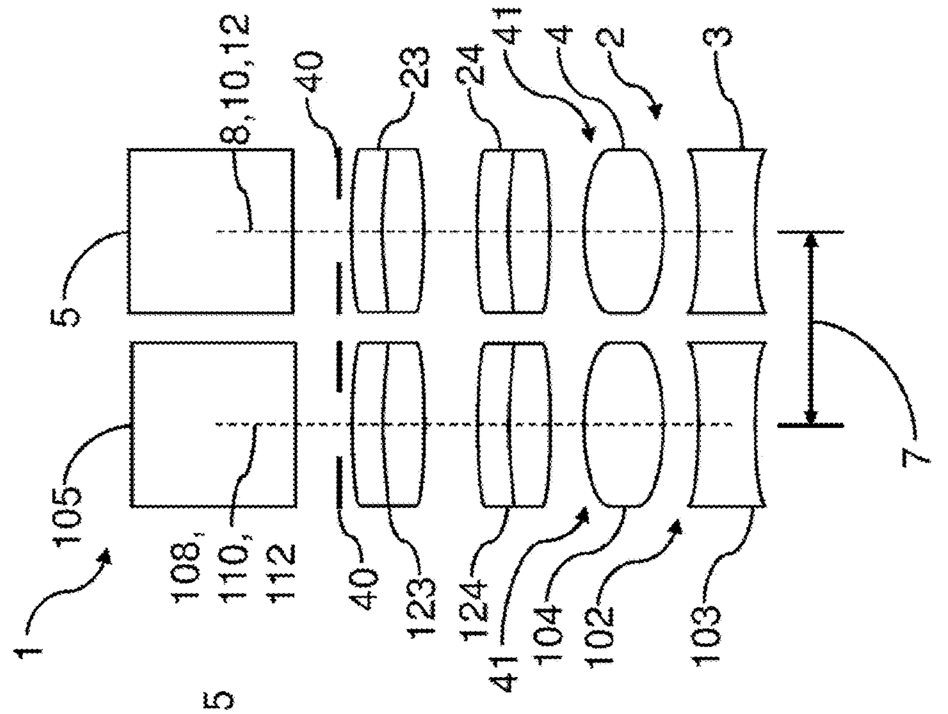
FIG. 6 shows a frontal view of the stereoscopic arrangement from FIG. 5.

FIG. 6 shows a frontal view of the stereoscopic arrangement from FIG. 5, wherein it is possible to see in particular the separate objective units 2, 102 having separate lens groups 3, 4, 103, 104 and the separate deflection units 5, 105. The separate lens groups 23, 24, 123, 124 may also be seen in the optical paths 8, 108.

Figure 7:
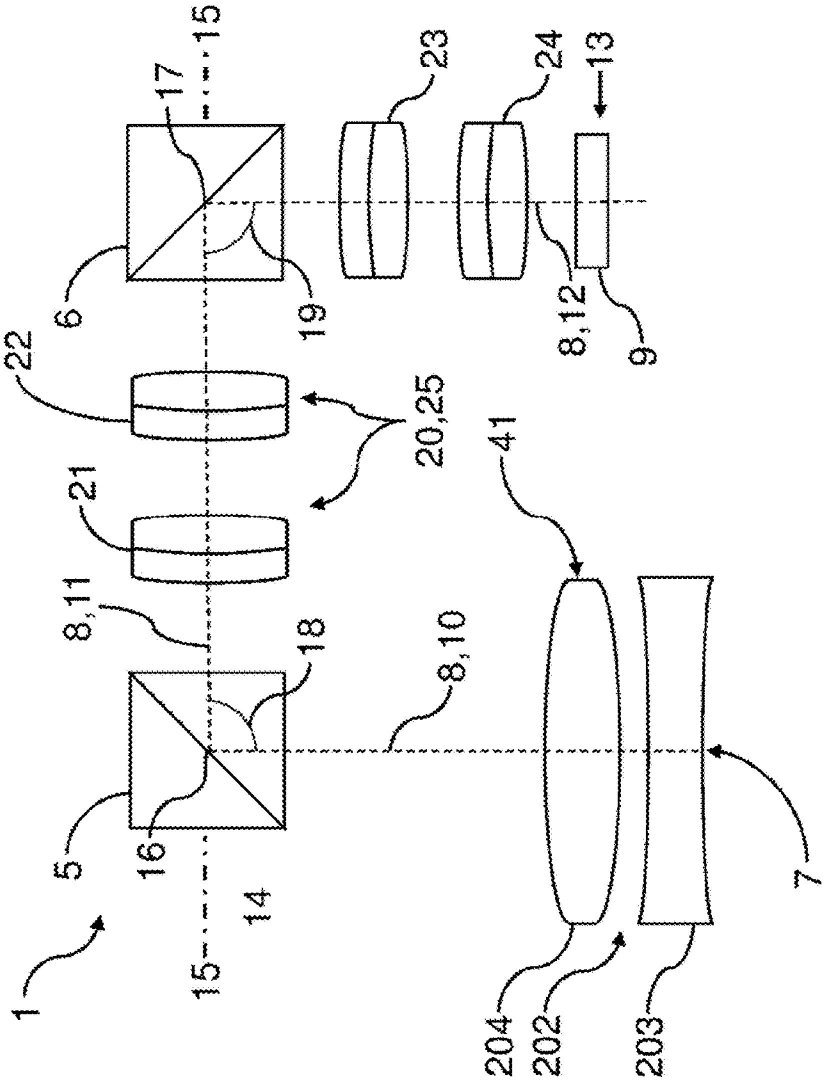
FIG. 7 shows a side view of a stereoscopic arrangement according to the invention.

FIG. 7 shows a side view of a further stereoscopic arrangement 1 according to the invention. In this exemplary embodiment, provision is made for a common objective unit 2 having common lens groups 3, 4, along with a further lens group 22 between the two deflection units 5, 6. Here, the lens groups 21 and 22 form a lens arrangement 20, which is a zoom lens 25 for changing the image section.

Figure 8:
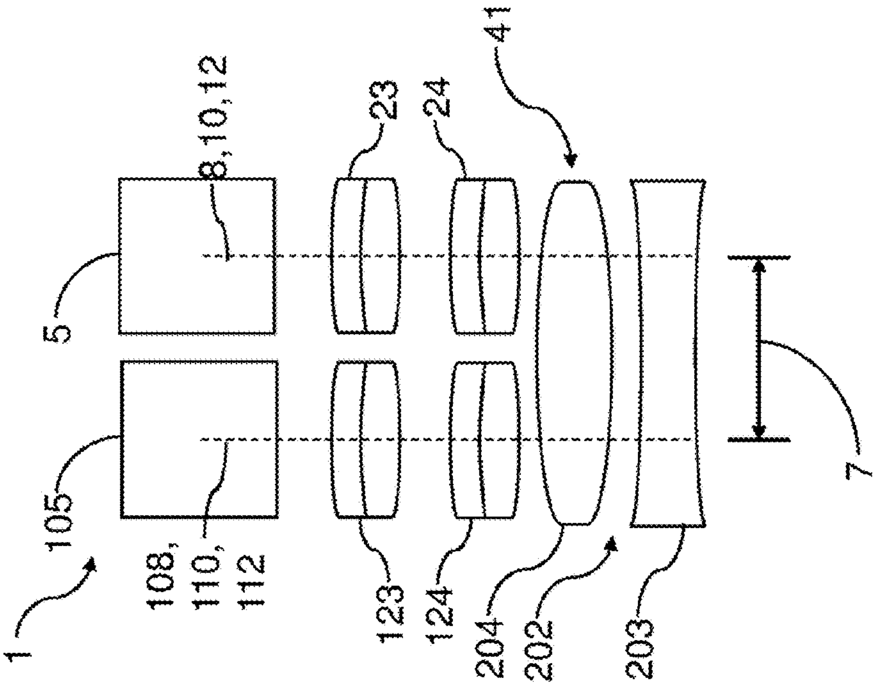
FIG. 8 shows a frontal view of the stereoscopic arrangement from FIG. 7.

FIG. 8 shows a frontal view of the stereoscopic arrangement 1 from FIG. 7, wherein it is possible to see the common objective unit 2 having common lens groups 3, 4, the separate deflection units 5, 105, and the separate lens groups 23, 24, 123, 124 in the optical paths 8, 108.

Figure 9:
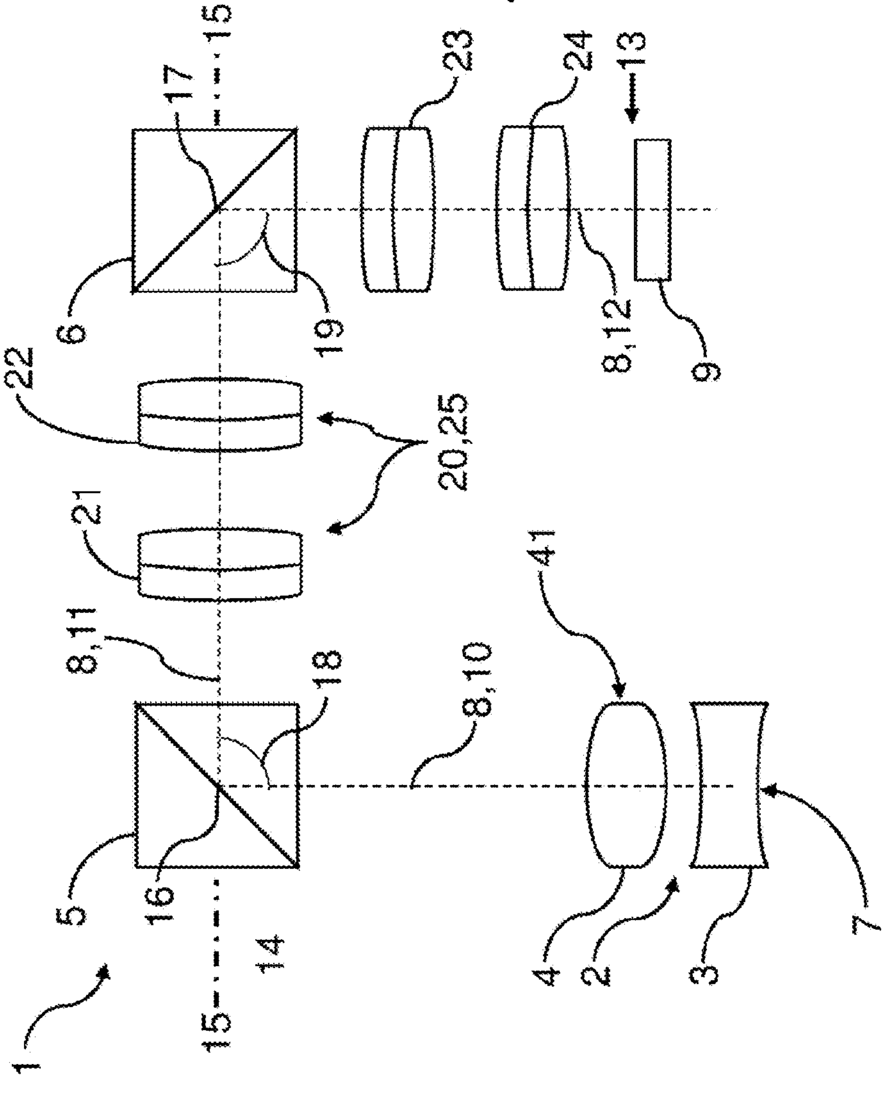
FIG. 9 shows a side view of a stereoscopic arrangement according to the invention.

FIG. 9 shows a side view of a further stereoscopic arrangement 1 according to the invention, which differs from the stereoscopic arrangement shown in FIG. 7 at least in that, in this exemplary embodiment, separate objective units 2, 102 having separate lens groups 3, 4, 103, 104 are provided for each optical path 8, 108.

Figure 10:
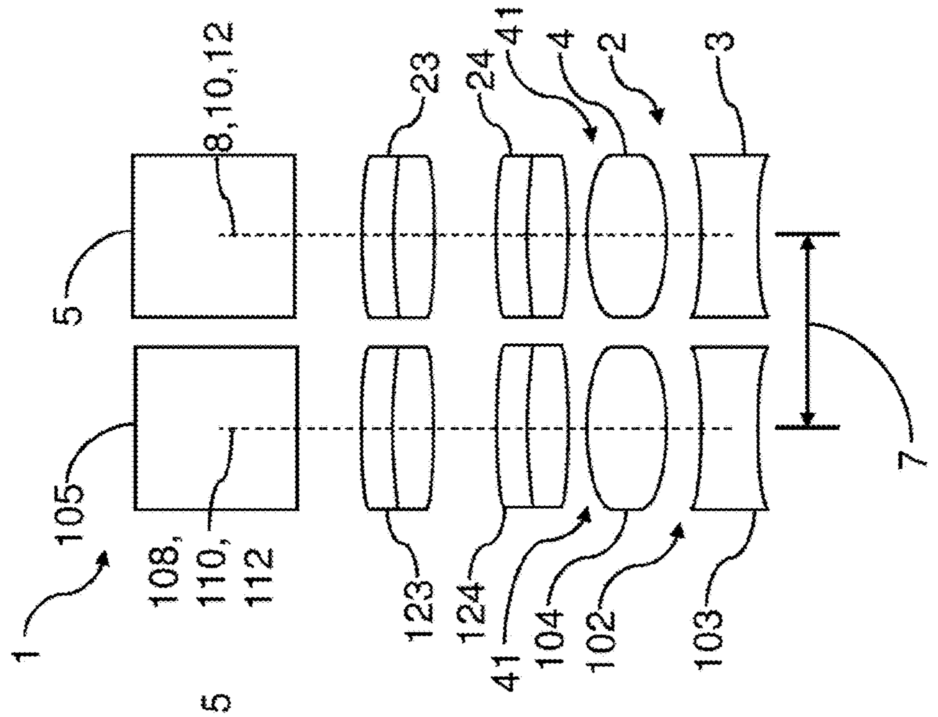
FIG. 10 shows a frontal view of the stereoscopic arrangement from FIG. 9.

FIG. 10 shows a frontal view of the stereoscopic arrangement 1 from FIG. 9, wherein it is possible to see the separate objective units 2, 102 having separate lens groups 3, 4, 103, 104, and also separate lens groups 23, 24, 123, 124 and separate deflection units 5, 105.

Figure 11:
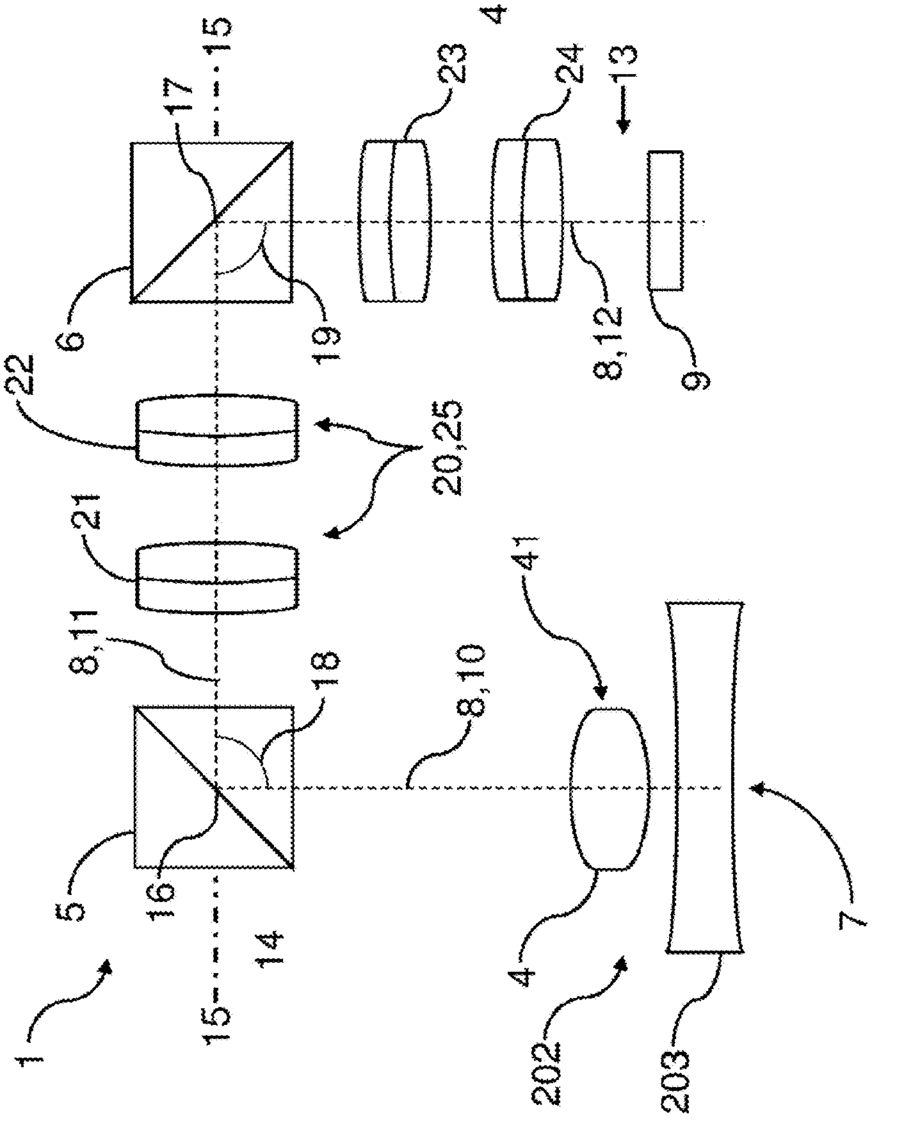
FIG. 11 shows a side view of a stereoscopic arrangement according to the invention.

FIG. 11 shows a side view of a further stereoscopic arrangement 1 according to the invention, which differs from the stereoscopic arrangement shown in FIG. 9 at least in that the objective unit 202 has a common lens group 203 but separate lens groups 4, 104.

Figure 12:
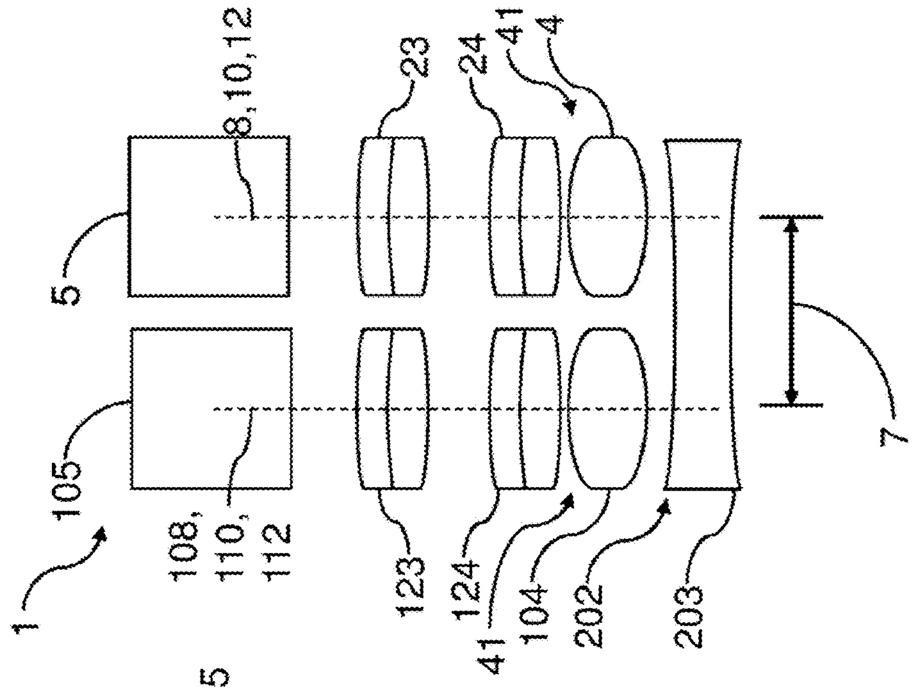
FIG. 12 shows a frontal view of the stereoscopic arrangement from FIG. 11.

FIG. 12 shows a frontal view of the stereoscopic arrangement 1 from FIG. 11, wherein it is possible to see in particular the common lens group 203 of the objective unit 202 and the separate lens groups 4, 104.

Figure 13:
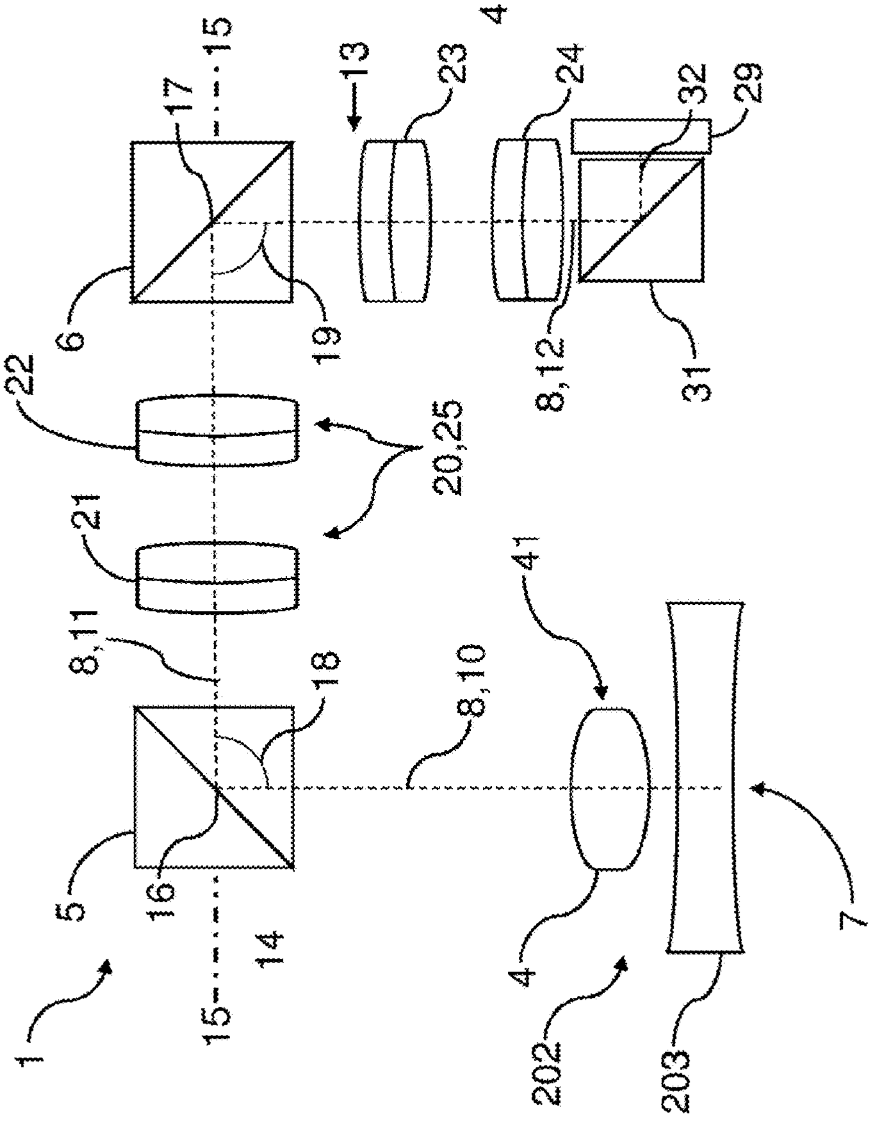
FIG. 13 shows a side view of a stereoscopic arrangement according to the invention.

FIG. 13 shows a side view of a further stereoscopic arrangement 1 according to the invention, wherein a further deflection unit 31 is provided here in the optical path 12. A further sub-path 32 leads therefrom to an image sensor 29.

Figure 14:
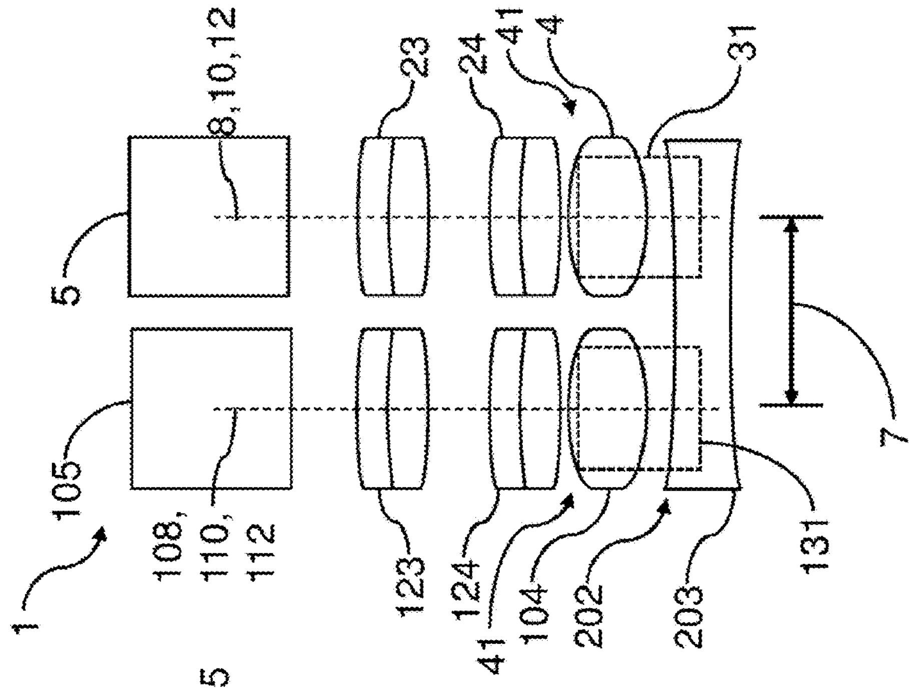
FIG. 14 shows a frontal view of the stereoscopic arrangement from FIG. 13.

FIG. 14 shows a frontal view of the stereoscopic arrangement from FIG. 13, wherein it is possible to see in particular the deflection units 31, 131, partially obscured by the objective unit 202, namely by the common lens group 203 and the separate lens groups 4, 104, in the respective optical paths 8, 108.

Figure 15:
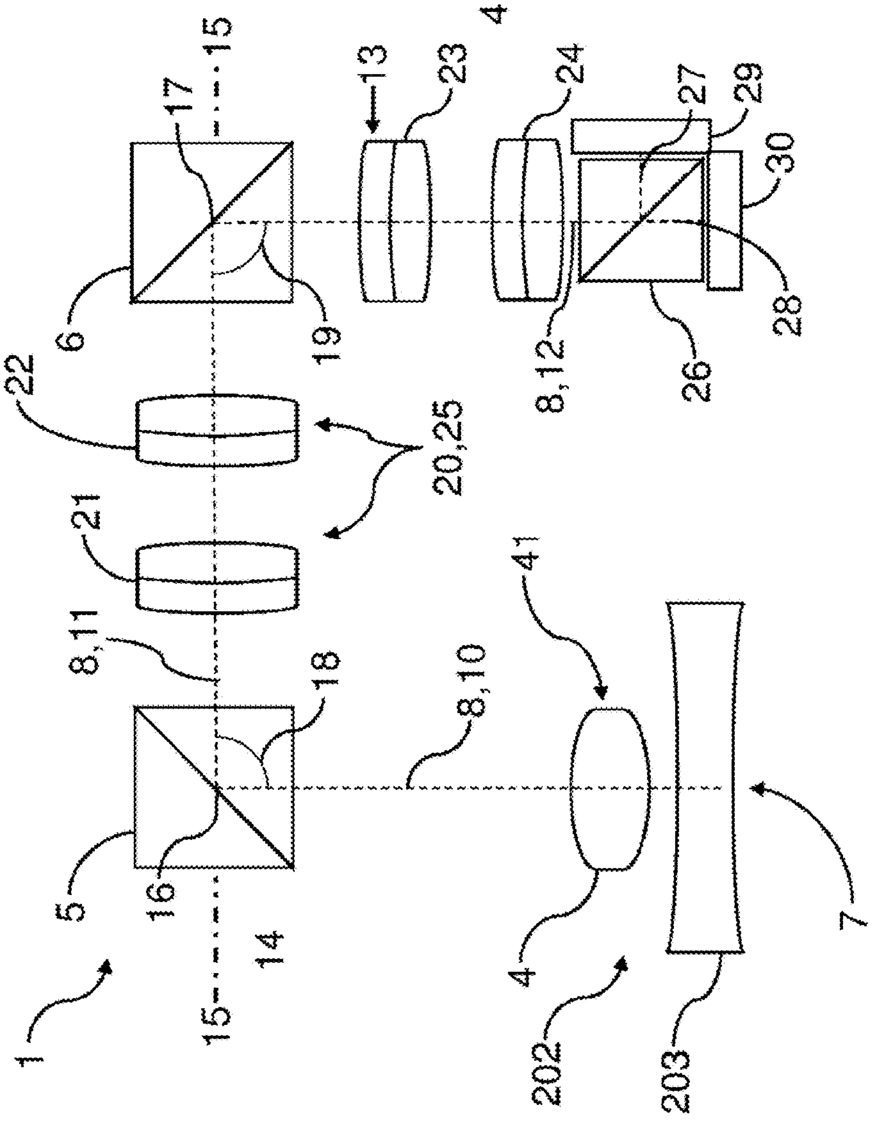
FIG. 15 shows a side view of a stereoscopic arrangement according to the invention.

FIG. 15 shows a side view of a further stereoscopic arrangement 1 according to the invention, wherein a further image sensor 30 is provided here in the vicinity of the beam splitter 26, to which further image sensor a partial beam 28 leads.

Figure 16:
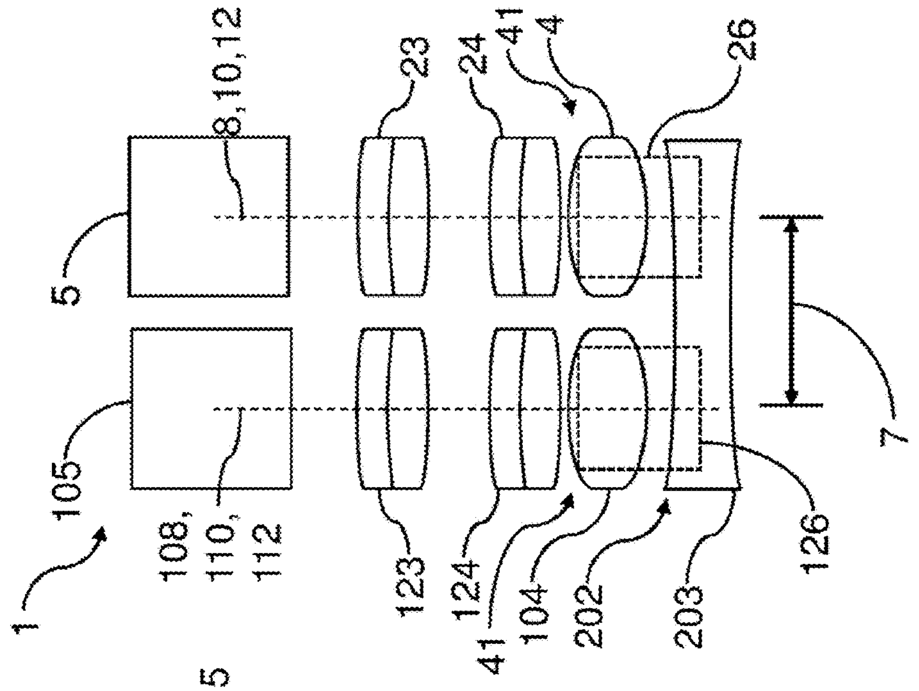
FIG. 16 shows a frontal view of the stereoscopic arrangement from FIG. 15.

FIG. 16 shows a frontal view of the stereoscopic arrangement 1 from FIG. 15, wherein it is possible to see in particular the beam splitters 26, 126, partially obscured by the objective unit 202, namely by the common lens group 203 and the separate lens groups 4, 104, in the respective optical paths 8, 108.

Figure 17:
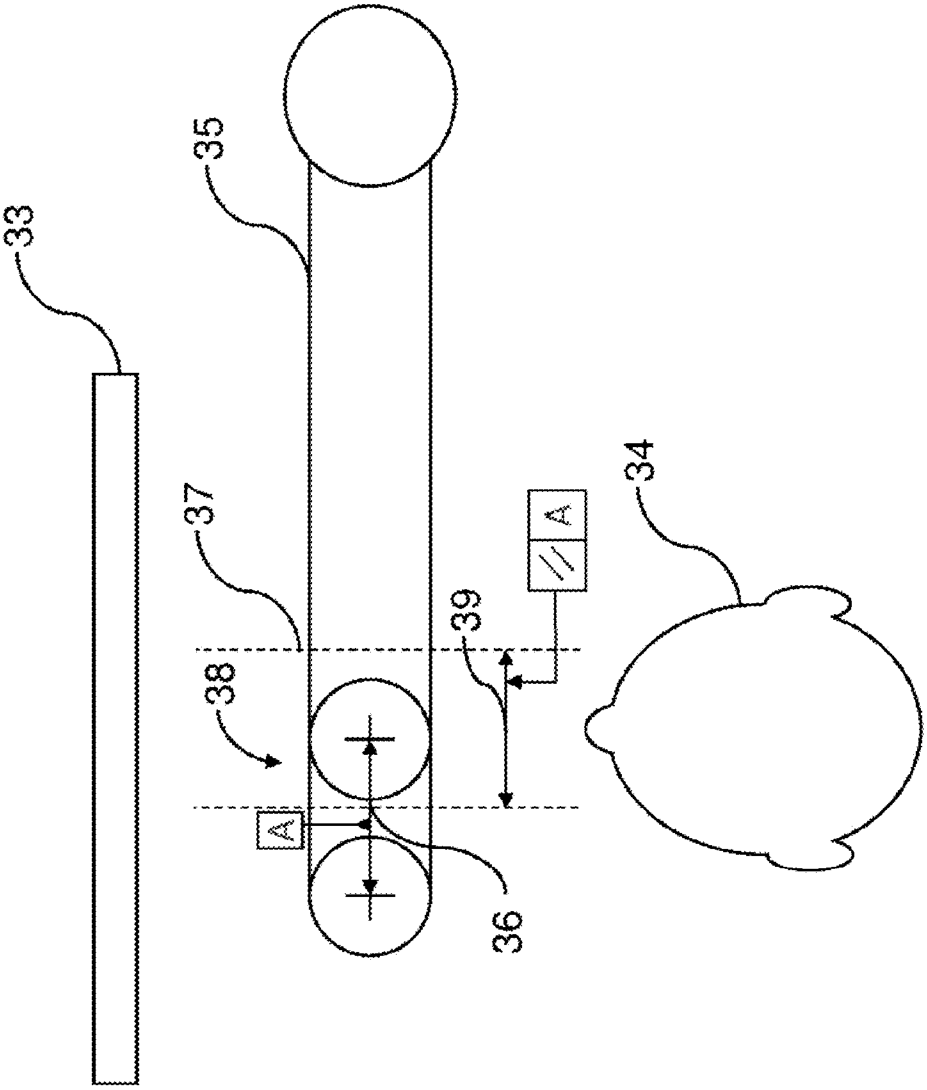
FIG. 17 shows a plan view of a surgical kit according to the invention.

FIG. 17 schematically illustrates the components of a surgical kit according to the invention, which comprises a stereoscopic arrangement 1 (as described above), a screen 33 and a robot arm 35, which is designed to be able to pivot about two axes. Using the robot arm 35 to which the arrangement 1 is attached, it is possible to change both a viewing direction of the stereoscopic arrangement, more precisely of its objective unit 2, and a working distance (that is to say the distance between the objective unit 2 and the observed object/operating area).

FIG. 17 also shows a plan view of a surgeon 34, who is looking at a live image, recorded using the arrangement 1, on a monitor in the form of a screen 33. The screen 33 may thus be used to display a live video image data stream currently being recorded using the arrangement 1.

In order always to obtain a sharp image even at different viewing angles and/or different working distances (=distance between the objective unit 2 and the object under observation), the system has an autofocus, which is implemented with the aid of a focus unit of the stereoscopic arrangement 1.

The length of the stereoscopic base 36 of the stereoscopic arrangement 1 corresponds in this case to the inter-eye distance 39 of the surgeon 34, that is to say the lateral distance between the two optical paths is selected according to a typical average value for the inter-eye distance 39 (see for instance FIG. 1 or FIG. 9).

In the view of FIG. 17, the robot arm 23 in this case conceals the guidance of the optical paths 11, 111 parallel to the stereoscopic base 36 and to the side away from the line of sight 37 between the surgeon 34 and the screen 33. In other words, those optical paths that run between the respective deflection element and the respective image sensor are thus guided away in the lateral direction, specifically exactly in the plane that is defined by the two paths and in which plane the stereoscopic base 36 is also located (see FIG. 1 or for example FIG. 9). Specifically, the invention has recognized that such a lateral installation space that does not impair the line of sight 37 may be used for the arrangement of the imaging optical elements, without the clear view of the surgeon 34 to the screen 33 thus being obstructed.

LIST OF REFERENCE SIGNS

1 stereoscopic arrangement
2 objective unit
3 lens group
4 lens group
5 deflection unit
6 deflection unit
7 stereoscopic base
8 optical path
9 image sensor

10 sub-path
11 sub-path
12 sub-path
13 projection direction
14 half-space
15 auxiliary plane
16 point of incidence
17 point of incidence
18 deflection angle
19 deflection angle
20 lens arrangement
21 lens group
22 lens group
23 lens group
24 lens group
25 zoom lens
26 beam splitter
27 sub-beam
28 sub-beam
29 image sensor
30 image sensor
31 deflection unit
32 sub-path
33 screen
34 surgeon
35 robot arm
36 stereo base
37 line of sight
38 surgical microscope
39 inter-eye distance
40 aperture stop
41 focus unit
102 objective unit
103 lens group
104 lens group
105 deflection unit
106 deflection unit
108 optical path
109 image sensor
110 sub-path
111 sub-path
112 sub-path
123 lens group
124 lens group
126 beam splitter
131 deflection unit
202 common objective unit
203 common lens group
204 common lens group
205 common deflection unit
206 common deflection unit
209 common image sensor

The invention claimed is:

1. A stereoscopic arrangement (1), comprising at least one objective unit (2, 102, 202);

at least one deflection unit (5, 6, 105, 106, 205, 206);

at least one image sensor (9, 29, 30), which is arranged downstream of the at least one deflection unit (5, 6, 105, 106, 205, 206) with respect to an optical path (8, 108) beginning at a stereoscopic base (7); and a first sub-path (10, 110) of the optical path (8, 108), which runs from the objective unit (2, 102, 202) to the at least one deflection unit (5, 6, 105, 106, 205, 206) and a further sub-path (11, 12, 111, 112) of the optical path (8, 108), which ends at the at least one image sensor (9, 29, 30), run in opposite directions.

2. The stereoscopic arrangement (1) as claimed in claim 1, wherein a projection direction (13) of the further sub path is aligned at an angle with respect to the first sub-path (10, 110) of the optical path (8, 108).

3. The stereoscopic arrangement (1) as claimed in claim 1, further comprising:

an image sensor (9, 29, 30) arranged in a half-space (14) containing the objective unit (2, 102, 202), the half-space being delimited by an auxiliary plane (15) containing the deflection unit (5, 6, 105, 106, 205, 206) and aligned orthogonally to the first sub-path (10, 110) of the optical path (8, 108).

4. The stereoscopic arrangement (1) as claimed in claim 3, wherein the auxiliary plane (15) runs through a point of incidence (16, 17) of the optical path (8, 108) on the deflection unit (5, 6, 105, 106, 205, 206).

5. The stereoscopic arrangement (1) as claimed in claim 3, wherein at least one lens group (21, 22, 23, 24, 123, 124) of a lens arrangement (20) is formed in the further sub-path (11, 111) running in the auxiliary plane.

6. The stereoscopic arrangement (1) as claimed in claim 1, wherein two optical sub-paths (8, 108) are formed, running from the at least one deflection unit (3, 103, 203) to a respective one of the image sensors (9, 109), and a respective optical lens or lens group (21, 22) is arranged in each of the two sub- paths (8, 108), said lens or lens group being arranged spaced from the at least one deflection unit (3, 103, 203) and spaced from the respective image sensor (9, 109) and at least one of the position or orientation of said optical lens or lens group relative to the associated deflection unit (3, 103, 203) and relative to the associated image sensor (9, 109) is adjustable.

7. The stereoscopic arrangement (1) as claimed in claim 6, wherein a respective setting means is formed so as to adjust the at least one of the position or orientation of the respective optical lens or lens group (21, 22), or the at least one of the position or orientation, which is adjusted and optimized once, of the respective optical lens or lens group (21, 22) is permanently fixed.

8. The stereoscopic arrangement (1) as claimed in claim 1, wherein there are at least two of the deflection units (5, 6, 105, 106, 205, 206) aligned such that their deflection angles (18, 19) define a same direction of rotation.

9. The stereoscopic arrangement (1) as claimed in claim 1, wherein at least one lens group (21, 22, 23, 24, 123, 124) of a lens arrangement (20) is formed in the optical path (8, 108) between the deflection unit (5, 6, 105, 106, 205, 206) and the objective unit (2, 102, 202).

10. The stereoscopic arrangement (1) as claimed in claim 1, further comprising:

a lens arrangement (20) that forms a zoom lens (25), wherein the deflection unit (5, 6, 105, 106, 205, 206) is located between at least two lens groups (21, 22, 23, 24, 123, 124) of the zoom lens (25), and the respective deflection unit (5, 6, 105, 106, 205, 206) connects two of the optical sub-paths (11, 12/111, 112) that run through the zoom lens (25), but in different spatial directions.

11. The stereoscopic arrangement (1) as claimed in claim 10, wherein the at least one lens group (21, 22, 23, 24, 123, 124) of the zoom lens (25) is located in a sub-path (11, 12, 111, 112), running away from the auxiliary plane (15), of the optical path (8, 108), and the at least one lens group (21, 22, 23, 24, 123, 124) of the zoom lens (25) is located in the first sub-path (10, 110), running towards the auxiliary plane (15), of the optical path (8, 108).

12. The stereoscopic arrangement (1) as claimed in claim 1, wherein at least one separate one of the objective units (2, 102) and/or one separate one of the deflection units (5, 6, 105, 106) and/or one separate lens group (21, 22, 23, 24, 123, 124) of a lens arrangement (20) and/or one separate one of the image sensors (9, 29, 30) is provided for each said optical path (8, 108).

13. The stereoscopic arrangement (1) as claimed in claim 1, wherein at least one common one of the at least one objective unit (202) and/or one common one of the at least one deflection unit (205, 206) and/or one common lens group (203, 204) of a lens arrangement and/or one common one of the at least one image sensor (209) is provided for the optical paths (8, 108).

14. The stereoscopic arrangement (1) as claimed in claim 1, further comprising at least one beam splitter (26, 126) located in the at least one optical path (8, 108), and a separate one of the image sensors (29, 30) is arranged in each sub-beam (27, 28) leaving the beam splitter (26, 126).

15. The stereoscopic arrangement (1) as claimed in claim 1, further comprising at least one focus unit (41) arranged upstream of the at least one deflection unit (5, 6, 105, 106, 205, 206) in the beam path, and via the focus unit it is possible to change a position of a focus plane of the stereoscopic arrangement (1).

16. The stereoscopic arrangement (1) as claimed in claim 1, further comprising:

at least one adjustable aperture stop (40) arranged downstream of the at least one objective unit (2, 102, 202) in the beam path, said aperture stop being configured to adjust at least one of a depth of field or an optical resolution, or two of the optical paths are formed, running from the at least one deflection unit (5, 6, 105, 106, 205, 206) to a respective one of the image sensors (9, 29, 30), and a respective one of the adjustable aperture stops (40) is arranged in each of the two optical paths.

17. A surgical microscope having a stereoscopic arrangement (1) as claimed in claim 1.

18. A surgical kit for use in surgical interventions, comprising:

the stereoscopic arrangement (1) as claimed in claim 1, a screen (33) for displaying a stereoscopic image that has been recorded with the stereoscopic arrangement (1), wherein the screen (33) is arranged behind the stereoscopic arrangement (1) such that a surgeon (34) looking at the screen (33) in order to observe a patient with the aid of the stereoscopic arrangement (1) has a clear view of the screen (33), and a movable robot arm (35), wherein the stereoscopic arrangement (1) is attached to the robot arm (23) so as to be able to pivot such that it is possible to change a viewing angle of the stereoscopic arrangement (1), wherein the stereoscopic arrangement (1) is aligned such that a stereoscopic base (36) of the stereoscopic arrangement (1) runs parallel to the screen (26) and such that the optical paths (5, 105) of the stereoscopic arrangement (1) are guided away parallel to the stereoscopic base (4) and to the side with respect to a line of sight (28) between the surgeon (25) and the screen (26).

19. The surgical kit as claimed in claim 18 wherein there are two of the sub-paths (7, 107) of the stereoscopic arrangement (1), which run between the at least one deflection unit (3, 103, 203) and the least one image sensor (6, 106), which are arranged above one another with respect to the sub-path (8, 108), running between the objective unit (2, 102, 202) and the at least one deflection unit (3, 103, 203), of the stereoscopic arrangement (1), or run in opposite directions.

20. The stereoscopic arrangement (1) as claimed in claim 1, wherein at least one lens group (21, 22, 23, 24, 123, 124) of a lens arrangement (20) is formed in the optical path (8, 108) between the deflection unit (5, 6, 105, 106, 205, 206) and the image sensor (9, 29, 30).

* * * * *